(12) United States Patent
Biswas et al.

(10) Patent No.: US 10,571,324 B2
(45) Date of Patent: *Feb. 25, 2020

(54) SYSTEM AND METHODS FOR A SMART WATER BOTTLE CONVERTER

(71) Applicant: BOARD OF TRUSTEES OF MICHIGAN STATE UNIVERSITY, East Lansing, MI (US)

(72) Inventors: Subir Biswas, East Lansing, MI (US); Bo Dong, East Lansing, MI (US); Ryan Gallant, East Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 81 days.

This patent is subject to a terminal disclaimer.

(21) Appl. No.: 15/987,012

(22) Filed: May 23, 2018

(65) Prior Publication Data

US 2018/0266866 A1    Sep. 20, 2018

Related U.S. Application Data

(63) Continuation of application No. 14/793,266, filed on Jul. 7, 2015.

(Continued)

(51) Int. Cl.
*G01F 11/00* (2006.01)
*A47G 19/22* (2006.01)
(Continued)

(52) U.S. Cl.
CPC .............. *G01F 11/00* (2013.01); *A47G 19/22* (2013.01); *A47G 23/10* (2013.01);
(Continued)

(58) Field of Classification Search
CPC ......... G01B 21/20; G01B 21/22; G01F 23/00; G01F 11/00; G01F 15/063;
(Continued)

(56) References Cited

U.S. PATENT DOCUMENTS 5,727,908 A    3/1998  Ward
6,036,055 A    3/2000  Mogadam et al.
(Continued)

OTHER PUBLICATIONS

Dong, Bo et al., "A self-monitoring water bottle for tracking liquid intake," Healthcare Innovation Conference (HIC), 2014 IEEE, pp. 311-314, Oct. 2014.

(Continued)

*Primary Examiner* — Jarrett J Stark
(74) *Attorney, Agent, or Firm* — Marshall, Gerstein & Borun LLP (57) ABSTRACT

A method and system may track liquid consumption by a user from a liquid container using a flexible, network-connected, smart band. The smart band may detect orientations of the liquid container and identify sips taken by a user based on a pattern in the detected orientations. The smart band may also estimate a liquid consumption metric based on characteristics of the identified sips such as the duration of the sip. The identified sip as well as sip characteristics and the liquid consumption metric may be displayed on the smart band, and also may be transmitted to a server for storage and for display on another network-enabled device.

16 Claims, 7 Drawing Sheets

Related U.S. Application Data (60) Provisional application No. 62/021,430, filed on Jul. 7, 2014.

(51) Int. Cl.
  *G06Q 50/24*  (2012.01)
  *A47G 23/10*  (2006.01)
  *G01F 23/00*  (2006.01)
  *G16H 20/10*  (2018.01)
  *G01F 22/00*  (2006.01)

(52) U.S. Cl.
  CPC ......... *G01F 23/0076* (2013.01); *G06Q 50/24* (2013.01); *G16H 20/10* (2018.01); *G01F 22/00* (2013.01)

(58) Field of Classification Search
  CPC ... G01F 15/0755; G01P 15/00; A61B 5/4875; A47G 23/10; A47G 23/16; G06Q 50/24; Y02A 90/26; Y10T 137/7837
  See application file for complete search history.

(56) References Cited

U.S. PATENT DOCUMENTS

| | | | |
|---|---|---|---|
| 6,504,481 | B2 | 1/2003 | Teller |
| 8,608,026 | B1 | 12/2013 | Temko et al. |
| 2005/0210979 | A1* | 9/2005 | Urano .................. G01C 9/06 73/514.09 |
| 2007/0205203 | A1 | 9/2007 | Temko |
| 2009/0178479 | A1* | 7/2009 | Pagovich ............ G01F 19/00 73/323 |
| 2011/0180563 | A1 | 7/2011 | Fitchett et al. |
| 2011/0217681 | A1* | 9/2011 | Krejcarek .......... G06F 19/3481 434/236 |
| 2011/0309103 | A1 | 12/2011 | Heatherly et al. |
| 2012/0094261 | A1* | 4/2012 | Hayn .................... A47G 23/16 434/247 |
| 2014/0372045 | A1* | 12/2014 | Keski-Pukkila ..... A61B 5/6887 702/19 |
| 2015/0335184 | A1* | 11/2015 | Balachandran .... A47G 19/2288 219/438 |
| 2016/0003615 | A1* | 1/2016 | Biswas ............... G01F 23/0076 702/151 |
| 2018/0361040 | A1* | 12/2018 | O'Toole ................ A61M 1/062 |

OTHER PUBLICATIONS

Schols, J. M. G. A., et al. "Preventing and treating dehydration in the elderly during periods of illness and warm weather." JNHA—The Journal of Nutrition, Health and Aging 13.2, pp. 150-157, 2009.

Amft, Oliver, et al. "Towards wearable sensing-based assessment of fluid intake." Pervasive Computing and Communications Workshops (PERCOM Workshops), 2010 8th IEEE International Conference on. IEEE, 2010.

Chiu, Meng-Chieh, et al. "Playful bottle: a mobile social persuasion system to motivate healthy water intake." Proceedings of the 11th international conference on Ubiquitous computing. ACM, 2009.

Dong, Bo, et al. "A mobile food intake monitoring system based on breathing signal analysis." Proceedings of the 8th International Conference on Body Area Networks. ICST (Institute for Computer Sciences, Social-Informatics and Telecommunications Engineering), 2013.

Montoye, Alexander H., et al. "Use of a Wireless Network of Accelerometers for Improved Measurement of Human Energy Expenditure." Electronics 3.2, pp. 205-220, 2014.

Hall, Mark, et al. "The WEKA data mining software: an update." ACM SIGKDD explorations newsletter 11.1, pp. 10-18, 2009.

Huber, "ILUMI Smartbottle: The new way to keep hydrated," Kickstarter, Jul. 2013, <https://www.kickstarter.com/projects/thehubergroup/ilumi-bottle-the-new-way-to-keep-hydrated>.

Kooser, Amanda, "Smart Water Bottle Alerts You When It's time to Hydrate," CNET, Sep. 2013, <http://www.cnet.com/news/smart-water-bottle-alerts-you-when-its-time-to-hydrate>.

"Product: Technology," HyrdraCoach, <http://www.hydracoach.com/technology/index.html>.

Office Action for U.S. Appl. No. 14/793,266, dated Oct. 6, 2017.

* cited by examiner

SYSTEM AND METHODS FOR A SMART WATER BOTTLE CONVERTER

CROSS-REFERENCE TO RELATED APPLICATIONS

This application is a continuation of and claims priority to U.S. application Ser. No. 14/793,266 filed on Jul. 7, 2015, entitled "System And Methods For a Smart Water Bottle Converter," which claims priority to and the benefit of the filing date of U.S. Provisional Patent Application No. 62/021,430, filed on Jul. 7, 2014, entitled "Systems And Methods For A Smart Water Bottle Converter," the entire disclosures of each of which is hereby expressly incorporated by reference herein.

TECHNICAL FIELD

The present disclosure generally relates to a fluid intake tracking device and, more particularly, to systems and methods for determining a user's fluid intake using an adaptable liquid container sensor.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Today, many people, from busy professionals to the elderly, track their fluid intake for health reasons such as preventing dehydration. Further, athletes may track their fluid intake to ensure they are properly hydrated to prevent injuries and also to achieve peak performance levels. Proper water intake can help remove waste, maintain a proper electrolyte balance, and dissipate heat thereby regulating body temperature.

To date, few have proposed cost effective techniques for measuring fluid intake, and those that have been proposed require specialized water liquid containers and fluid contacting type sensors.

SUMMARY

To track the amount of liquid consumed by a user, a network-connected, flexible band (also referred to interchangeably herein as a "smart band" or a "smart band device") may be placed over the exterior of a liquid container, such as an ordinary water bottle, to convert the water bottle into a smart bottle. For example, the band may include an accelerometer as well as a transceiver (e.g., a Bluetooth radio, or any other short-range wireless network connection device), which enables the band to communicate fluid intake results to a smart phone or a centralized server.

The accelerometer may measure the orientations of the water bottle, and a computing device within the band may analyze the identified orientations to determine whether a user takes a sip from the bottle and statistics regarding sips. For example, the computing device may compare the measured orientations to a sip signature, which is a predetermined pattern of orientations which indicate that a sip has been taken. More specifically, to take a sip a user typically picks up a water bottle, orients the bottle toward her mouth, maintains roughly the same orientation while taking the sip, and then orients the water bottle in the upward position before placing the bottle down on a table or some other surface. This pattern may be used to define the sip signature.

By comparing subsequent measured orientations to the sip signature, the computing device may determine the amount of sips taken by a user over a particular time interval, as well as one or more characteristics of the sip, such as the length of time for each sip (e.g., by calculating the length of time that the bottle is most likely oriented toward the user's mouth). The number of sips taken and/or the sip characteristics may be displayed on a user interface on the smart band for a user to see. In some examples, the number of sips and/or the sip characteristics may be analyzed by the computing device to estimate a liquid consumption metric for the particular time interval. This estimated liquid consumption metric may be displayed on the smart band. Further, the number of sips, sip characteristics, and liquid consumption metric may be transmitted, via the Bluetooth (or other wireless) connection, to a network-enabled device which, in turn, may transmit the information to a centralized server for storage and further analysis.

In this manner, a user can measure her fluid intake from any liquid container (e.g., a bottle, a Thermos, a glass, a cup, etc.) by retrofitting the smart band over the exterior of the bottle. In addition to measuring her fluid intake, the user can measure her number of sips per unit time to reliably track and detect changes in her hydration habits. Moreover, by placing the smart band on the outside of the bottle, the smart band remains dry (i.e., out of contact with the liquid), and performance of the system is unlikely to degrade over time and/or require maintenance. Further, the user's fluid intake information may be stored at a centralized server allowing the user to access this information from several network-enabled devices in addition to the smart band.

In an embodiment, a method for tracking liquid consumption using a flexible, network-connected band is provided. The method includes detecting one or more orientations of a liquid container, identifying that a sip from the liquid container has been taken by a user based on the detected one or more orientations of the liquid container, and identifying one or more characteristics of the sip. The method further includes analyzing the identified sip and the one or more characteristics of the sip to determine an estimate of a liquid consumption metric for the user, and transmitting the identified sip and the one or more characteristics of the sip to one or more computing devices via a communication network for storage.

In another embodiment, a flexible, network-connected band mountable on exterior walls of a liquid container for tracking liquid consumption is provided. The band includes a hollow, cylindrically-shaped, flexible band removably attached to exterior walls of a liquid container, a communication interface, one or more processors disposed within the band and coupled to the communication interface, and a non-transitory computer-readable memory coupled to the one or more processors and storing instructions thereon. The instructions when executed by the one or more processors cause the band to detect an indication of one or more orientations of a liquid container, identify that a sip from the liquid container has been taken by a user based on the detected one or more orientations of the liquid container, and identify one or more characteristics of the sip. The instructions further cause the band to analyze the identified sip and the one or more characteristics of the sip to determine an estimate of a liquid consumption metric for the user, and transmit the sip identification information and the one or more characteristics of the sip to one or more computing devices via a communication network for storage.

BRIEF DESCRIPTION OF THE DRAWINGS

The figures described below depict various aspects of the system and methods disclosed therein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

DETAILED DESCRIPTION

Although the following text sets forth a detailed description of numerous different embodiments, it should be understood that the legal scope of the description is defined by the words of the claims set forth at the end of this patent and equivalents. The detailed description is to be construed as providing examples only and does not describe every possible embodiment since describing every possible embodiment would be impractical. Numerous alternative embodiments could be implemented, using either current technology or technology developed after the filing date of this patent, which would still fall within the scope of the claims.

Generally speaking, techniques for measuring a user's fluid intake may be implemented in a smart band device, one or more network-enabled devices, one or more network servers, or a system that includes a combination of these devices. However, for example purposes, the examples below focus primarily on an embodiment in which the orientations of a liquid container are measured and analyzed at the smart band device to determine fluid intake data such as an indication of a sip, characteristics of the sip, and/or an estimate of a liquid consumption metric for the sip. A liquid consumption metric may be an estimate of the volume of liquid consumed by the user, an estimate of the number of sips taken by a user over a time interval, when the sips where taken, the frequency of sips taken, etc. The fluid intake data may then be communicated to a network-enabled device (e.g., a device including a network interface for communicating information over a communication network) such as a smart phone, a laptop computer, a desktop computer, a wearable device, etc., via a Bluetooth or other short-range wireless connection. The network-enabled device may in turn communicate the fluid intake data to a centralized server such as a cloud server. The fluid intake data may then be stored at the centralized server and can be accessed by the user via the smart band device, or any other network-enabled device. Moreover, the fluid intake data for the user may be compared at the centralized server with other fluid intake data from other users to more accurately determine the sip signature. The sip signature may be an orientation pattern indicative of a sip of liquid taken by a user. For example, the sip signature may be determined by statistically analyzing orientation data for several sips taken by previous users and determining components of the orientation data which are the same or similar over the several sips. The fluid intake data for the user may also be compared with other fluid intake data from other users to estimate the user's liquid consumption metric. Updated sip signatures and liquid consumption metrics may then be transmitted to the smart band device, and used for determining future fluid intake data for the user.

In an example scenario, John Doe is training for a marathon and would like to drink about a half-gallon of water per day to stay properly hydrated. He may not have time to manually keep track of the amount he drinks and he may also use several different water bottles during his training sessions. To ensure John reaches his goal, he may attach one or more smart band devices to any of his several water bottles he uses during training. John may see the amount of water he is drinking on the display on the smart band device during his training sessions. Moreover, he may also view this data as well as further analyses on his drinking habits (e.g., day-to-day comparisons of his fluid intake, the time of day when he drinks the most, etc.) on his smart phone or another network-enabled device at the end of each day.

Figure 1:
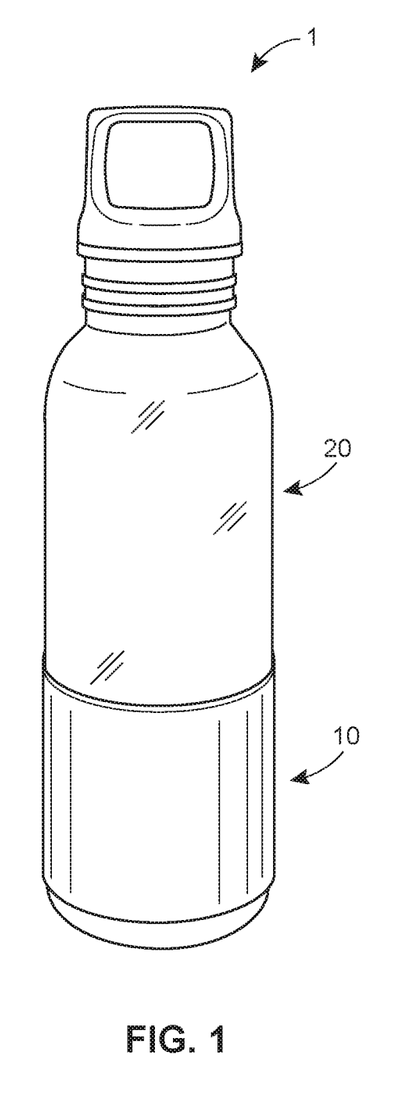
FIG. 1 illustrates a block diagram of an example smart band attached to a liquid container.

Referring to FIG. 1, an example smart bottle 1 includes a smart band device 10 which is removably attached to a liquid container 20. The smart band device 10 may be a hollow, cylindrically-shaped, flexible band containing a computing device having a user interface, one or more processors, a transceiver such as a Bluetooth radio, and an accelerometer disposed therein. The computing device within the smart band 10 is described in further detail below with reference to FIG. 2. Further, the smart band 10 may be made of an elastic material (e.g., rubber, nylon, polyurea, etc.) such that it may fit around several types of liquid containers. In some embodiments, the smart band 10 may fit around the base of the liquid container 20. Also, in some embodiments, during a training period, the smart band 10 may include a push-button switch. Users may press the push-button switch when they are taking sips and release the switch or press the switch again when they are finished taking sips to help train the smart band 10 to identify sips. While the liquid container 20 illustrated in FIG. 1 is a water bottle, the smart band device 10 may fit around any suitable type of liquid container such as a cup, a bottle, a Thermos, a glass, a canteen, etc. Moreover, the liquid container 20 may store any type of liquid such as water, juice, sports drinks including Gatorade®, Powerade®, or Vitaminwater®, tea, coffee, etc. The sip signatures are agnostic to the type of liquid in the bottle. The smart band 10 can be removed from the water bottle 20, and placed on another liquid container when the user chooses to drink from another source. In this manner, the smart band 10 can continue to measure the user's fluid intake even if the user switches liquid containers.

Figure 2:
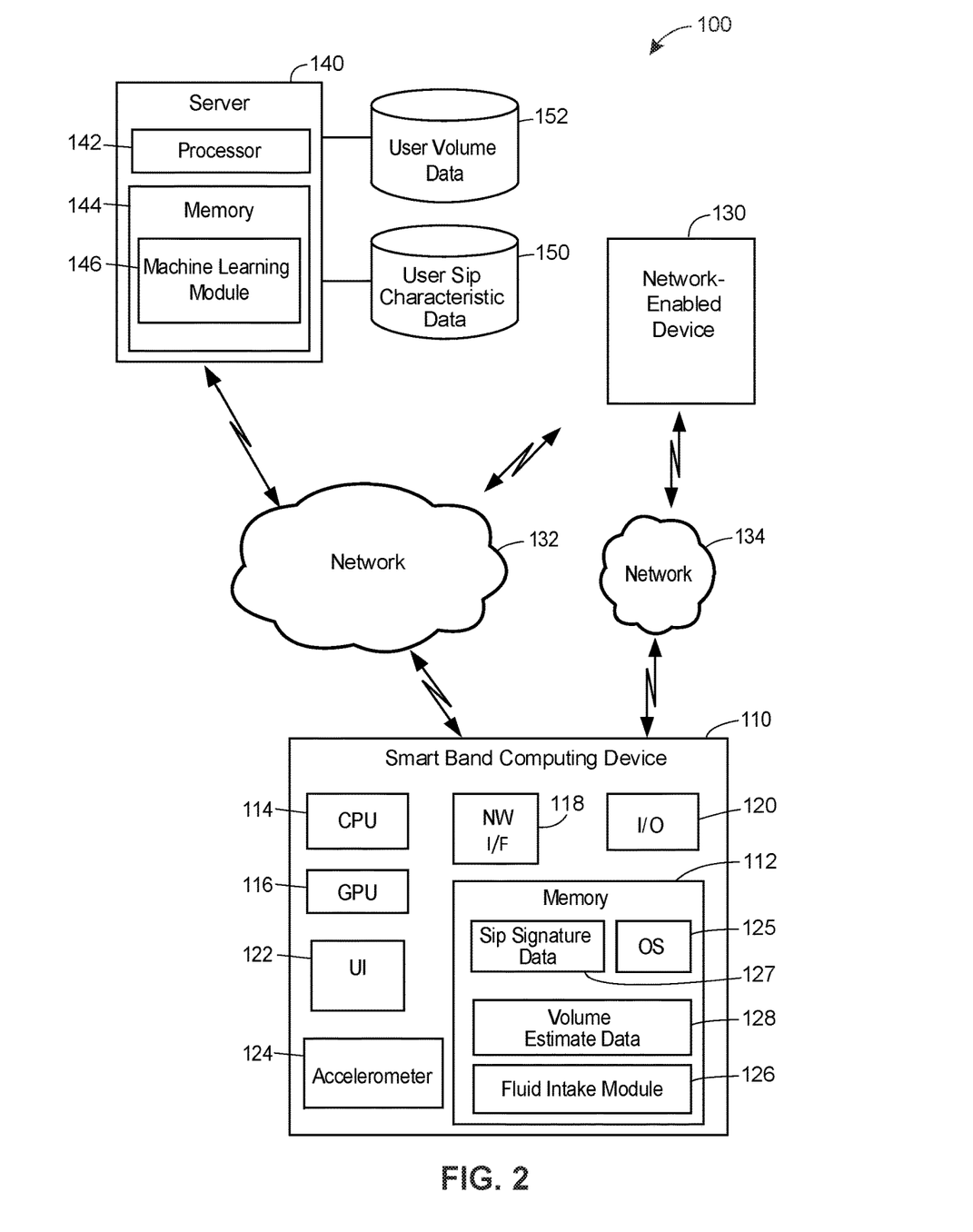
FIG. 2 illustrates a block diagram of an example communication system in which techniques for measuring fluid intake are implemented.

Turning to FIG. 2, an example communication system 100 in which the techniques outlined above can be implemented includes a smart band computing device 110 disposed within the smart band 10 of FIG. 1, one or more network-enabled devices 130, and a server 140. In an embodiment, the smart band computing device 110, the one or more network-enabled devices 130, and the server 140 may communicate over a communication network 132, which can be any suitable local or wide area network including a Wi-Fi network, a cellular network, the Internet, etc. In other embodiments, the network-enabled devices 130 and the server 140 may communicate over the communication network 132, and the smart band computing device 110 and one of the network-enabled devices 130 may communicate over a short-range wireless or wired network 134 such as a Bluetooth network. For example, the smart band computing device 110 may transmit and/or receive fluid intake data from one of the network-enabled devices 130 which has a Bluetooth connection. The network-enabled device 130 may then transmit and/or receive this data from the server 140, and as a result the fluid intake data may be viewed by a user on the smart band computing device 110, or on any of the network-enabled devices 130.

The network-enabled device 130 may include, for example, a tablet computer, a mobile device smart phone, a network-enabled cell phone, a laptop computer, a desktop computer, a wearable computing device, etc. Moreover, any other network-enabled device appropriately configured may interact with the communication system 100. Each of the network-enabled devices 130 may interact with the server 140 to receive web pages, application views or server data from the server 140 and may display the web pages, application views or server data via a user interface. For example, a smart phone may be connected to the smart band computing device 110 via a Bluetooth connection. The smart band computing device 110 may transmit fluid intake data to the smart phone which may transmit the data to the server 140. The user may later view the fluid intake data on, for example, a tablet computer by signing in to a login page.

In an example implementation, the smart band computing device 110 includes a memory 112, one or more processors (s) (CPU) 114, a graphic processing unit (GPU) 116, a network interface unit 118, and an I/O module 120. The smart band computing device 110 also includes a user interface (UI) 122 for viewing fluid intake data, and an accelerometer 124, such as a tri-axis accelerometer for measuring the orientations of the liquid container 20 surrounded by the smart band 10.

The memory 112 may be tangible, non-transitory memory and may include any types of suitable memory modules, including random access memory (RAM), read only memory (ROM), flash memory, other types of persistent memory, etc. The memory 112 stores an operating system (OS) 125 and one or more modules including a fluid intake module 126. The operating system 125 may be any type of suitable operating system such as modern smartphone operating systems, for example. Also, the I/O module 120 may be a touchscreen, for example.

The fluid intake module 126 may receive orientation data from the accelerometer 124 in order to perform a fluid intake analysis. For example, the fluid intake module 126 may compare the orientation data to sip signature data 127 which may be received from the server 140. The sip signature data 127 may include examples of sip signatures which may be used to determine whether a user has taken a sip from the liquid container 20. For example, sip signatures may be collected, during a training period, from orientation data measured when users press and/or release a push-button switch connected to the smart band 10 to indicate that they are taking sips. In any event, after determining that a sip has occurred, the fluid intake module 126 may also compare characteristics of the sip such as the length of time for the sip, the orientation data for the sip, etc., to volume estimate data 128 to estimate the volume of the liquid consumed based on the sip characteristics. The volume estimate data 128 may also be received from the server 140, and may include historical data (which may be collected during the training period) on the volume consumed for a sip corresponding to a particular set of sip characteristics. It will be appreciated that some of these components of the device 110 may be combined with others of these components, such as a single assembly housing the UI 122, GPU 116, and the I/O 120.

The server 140 may be a cloud based server, an application server, a web server, etc., and may include user sip characteristic data (e.g., recorded data from several users including the orientation patterns of a sip, the length of time for a sip, etc.), and user volume data (e.g., recorded data from several users including a comparison of the volume of sips to the length of the sip and orientation data for the sip, refill data, etc.) from a user sip characteristic database 150, and a user volume database 152, respectively. The server 140 then may provide the user sip characteristic data, and the user volume data to the smart band computing device 110 as part of the sip signature data 127 and the volume estimate data 128. The smart band computing device 110 may use this data to determine whether a user has taken a sip, characteristics of the sip, and/or a liquid consumption metric for the sip. In some embodiments, the user sip characteristic database 150 and the user volume database 152 may be disposed within the smart band computing device 110. The server 140 may also include a processor 142 which executes instructions from a computer-readable memory 144 to implement a machine learning module 146. The machine learning module 146 may extract the user sip characteristic data and the user volume data from several users and/or several liquid containers to determine a sip signature for calculating the amount of sips per unit time, and also to determine the volume consumed per sip. The machine learning module 146 detects sip events and volume consumed using the sip signature 127 and volume estimate data 128 with various machine learning techniques, such as artificial neural networks, support vector machines, naïve Bayes, random forests, boosting, linear regression, logistic regression, k-nearest neighbors, decision trees, hidden Markov models, etc. The data (e.g., a sip signature model) from the machine learning module 146 may be provided to the smart band computing device 110 as part of the sip signature data 127 and the volume estimate data 128. In other embodiments, the machine learning module 146 may be included in the memory 112 of the smart band computing device 110.

It will be understood that although the server 140 is illustrated in FIG. 2 as a single device, in general the server 140 can correspond to multiple servers responsible for respective types of content or respective operations. For example, a first server may collect, aggregate, and analyze fluid intake data from several users of several liquid containers to determine a sip signature, a volume estimate based on the sip, etc. Additionally, a second server may provide stored fluid intake data for a single user to a network-enabled device upon receiving login information for the user.

Figure 3A:
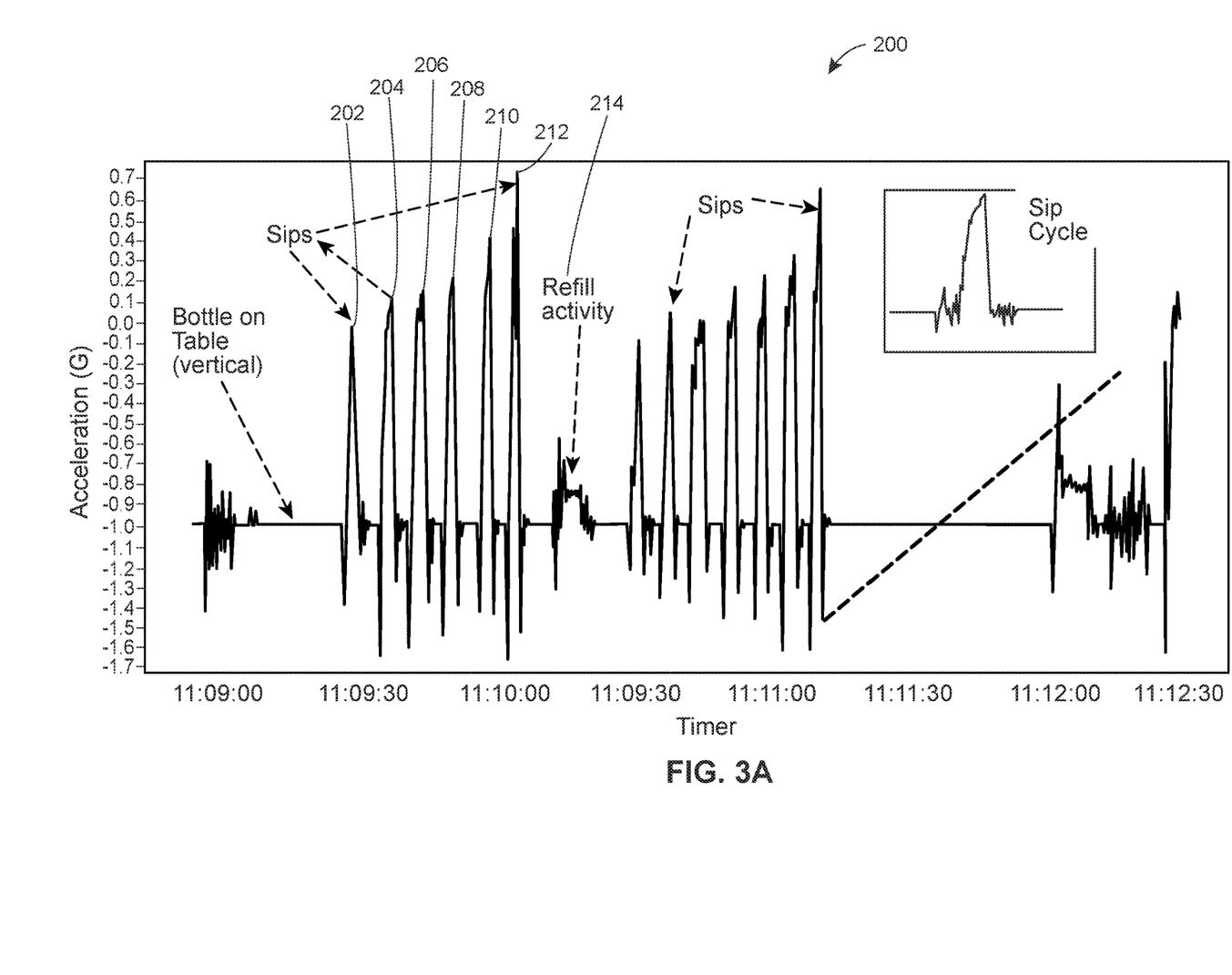
FIG. 3A illustrates a graph of example orientations of a liquid container including patterns indicative of a sip.

FIG. 3A illustrates example orientation data 200 measured by the accelerometer 124 of FIG. 2 and received by the fluid intake module 126. The orientation is measured based on the acceleration on the water bottle, or g-force, as a function of time. In an embodiment where the accelerometer 124 is a tri-axis accelerometer, the orientation data 200 may be measured on the y axis.

Figure 3B:
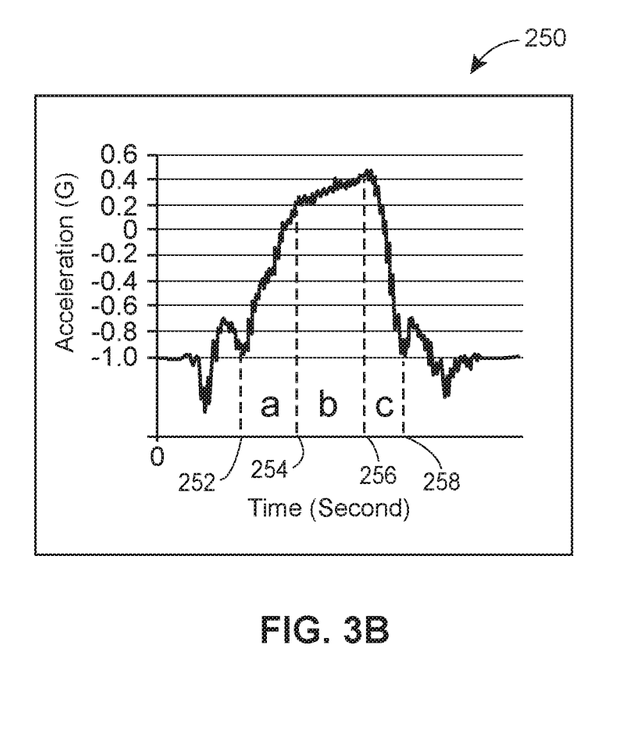
FIG. 3B illustrates a zoomed in portion of the example graph of FIG. 3A including a pattern indicative of a sip.
Figure 3C:
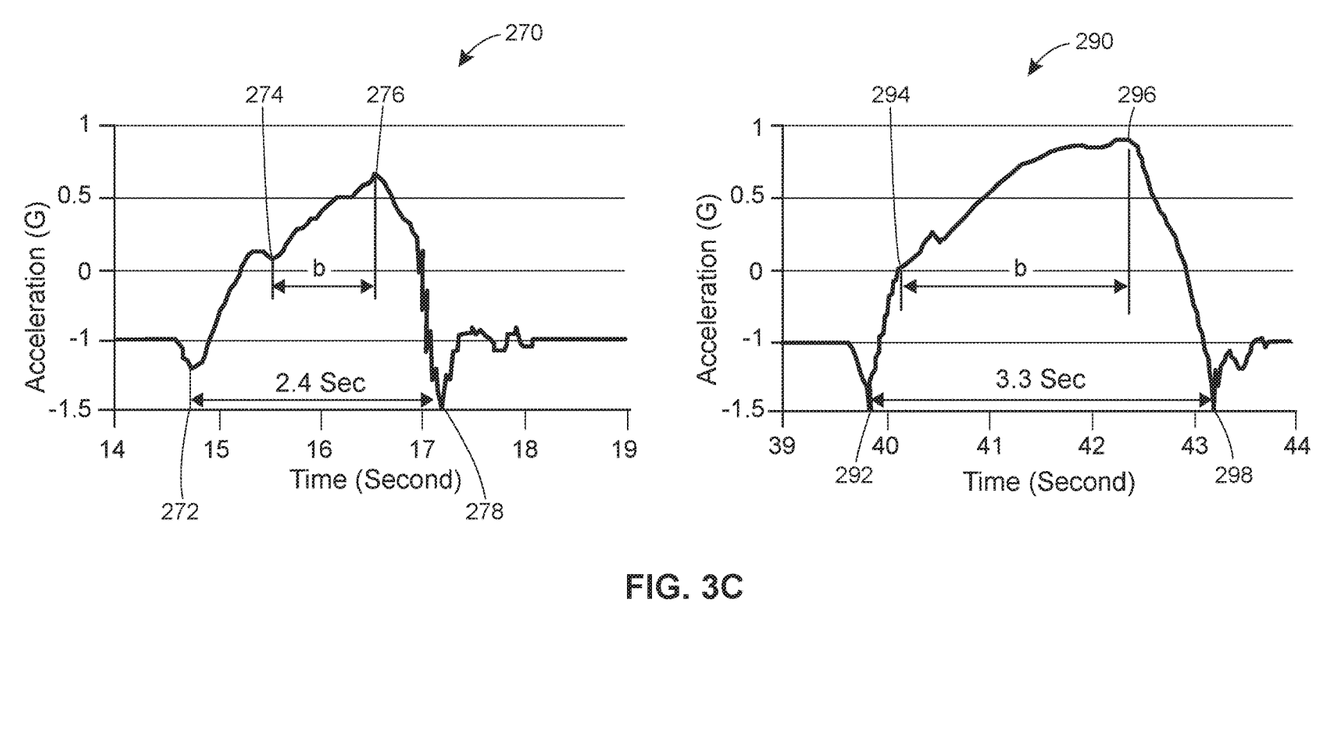
FIG. 3C illustrates example graphs including patterns indicative of a sip used to estimate volume consumed by a user.

In the example orientation data 200 of FIG. 3A, a water bottle in the vertical, upright position has a g-force of −1, a water bottle in the horizontal position has a g-force of 0, and a water bottle in the vertical, downright position has a g-force of +1. Accordingly, when the water bottle is tilted in the upright position such that it is no longer vertical but has not yet reached horizontal, the g-force will be between −1 and 0. Further, when the water bottle is tilted in the downright position such that it is no longer horizontal but has not yet reached downright, vertical, the g-force will be between 0 and +1. When a user takes a sip the bottle is most likely horizontal or tilted slightly downright from the horizontal position. Therefore, sips most likely occur when the g-force is at or above 0. Moreover, the closer the bottle is to empty, the more the user has to tilt the bottle to take a sip. As a result, as the bottle reaches empty, the g-force will approach +1 when the user takes a sip. However, this is merely an example manner in which the g-force may be calibrated. In some implementations, when the water bottle is in the vertical, upright position the g-force may be 0, and in other implementations the g-force may be +1 or any other suitable number. However, for clarity, FIGS. 3A-C illustrate example orientation data where a g-force of −1 indicates the water bottle is in the vertical, upright position.

The example orientation data 200 in FIG. 3A is measured from 11:09:00 AM until 11:12:30 AM. In this three and a half minute span, the user takes several sips. For example, from 11:09:00 until 11:10:30, the user takes six sips 202-212 and also refills the bottle 214. The first sip 202 has a maximum g-force or height of about 0 whereas the sixth sip 212 just before the refill event has a maximum g-force or height of about 0.7. This may indicate that for the first sip the user tilted the bottle horizontally, while for the sixth sip the user tilted the bottle about three quarters of the way down.

To identify a sip from the orientation data 200, the fluid intake module 126 may filter the orientation data to obtain sequences of orientation data which differ from the default vertical, upright orientation having a g-force of −1. For example, a filtered sequence of orientation data may include the first sip 202, because just before and just after the first sip the g-force is −1. Another filtered sequence of orientation data may be the refill event 214 or any of the second through sixth sips 204-212.

Each filtered sequence of orientation data may be compared to a sip signature to determine whether the filtered sequence is indicative of a sip. In some embodiments, the filtered sequences may also be compared to a refill signature to determine whether any of the filtered sequences are indicative of a refill. In any event, the sip signature may be an orientation pattern based on statistical data of previously recorded sips. The sip signature may include a height, a duration, an average orientation, etc. For example, based on the statistical data it may be improbable to take a sip in less than a half of a second. Therefore, the sip signature may include a minimum duration of a half second so that orientation data having a large peak (maximum g-force) but a short duration is not identified as a sip. In addition to determining whether the filtered sequence of orientation data is indicative of a sip, the fluid intake module 126 may also estimate a liquid consumption metric for the user during the sip. The sip identification and the liquid consumption metric estimation processes are described in more detail with reference to FIGS. 3B and 3C.

FIG. 3B illustrates an example filtered sequence of orientation data 250 similar to the fifth sip 210 of FIG. 3A. The filtered sequence of orientation data 250 may be separated into three parts denoted by "a," "b," and "c." During part "a," the bottle begins in the vertical, upright position 252, and is tilted downward past the horizontal position into a slightly downright position having a g-force of 0.2 (reference 254). This may be indicative of a user picking up the bottle and tilting the bottle toward her lips. In some embodiments, part "a" may be identified by a steep positive slope. During part "b," the bottle begins in the slightly downright position 254 and is gradually tilted downward to a slightly further downright position of about 0.5 (reference 256). This may be indicative of a user sipping from the bottle and tilting the bottle slowly so that water can constantly flow into her mouth. In some embodiments, part "b" may be identified by a change in slope in the orientation, from the steep positive slope in part "a" to a more gradual slope. During part "c," the bottle begins in the slightly further downright position 256 and is tilted upward to the vertical, upright position 258. In some embodiments, part "c" may be identified by yet another change in slope in the orientation, from the gradual slope in part "b" to a steep negative slope.

To determine whether this sequence is indicative of a sip, one or more components of the filtered sequence of orientation data 250 may be compared to the sip signature. The sip signature may include parts "a," "b," and "c," and for a filtered sequence to have a matching sip signature, the filtered sequence may need to include a positive orientation slope followed by a more gradual, nearly constant slope, followed by a negative orientation slope. Additionally, for example, the height or maximum g-force of the filtered sequence of orientation data 250 may be compared to the sip signature. In some scenarios, the sip signature may have a minimum height of 0 such that the bottle must be tilted at least horizontally before a filtered sequence can be identified as a sip. Moreover, the duration and slope of part "b" may also be an important factor for identifying a sip. For example, if the change in orientation does not level off between parts "a" and "b" as it does in FIG. 3B, then it becomes less likely that the user took a sip. In order to take a sip, the user most likely has to stop tilting the bottle or gradually tilt the bottle to take a drink. However, these are merely example sip characteristics which may be a part of the sip signature. The sip signature may include additional sip characteristics and/or factors or may not include some of the characteristics described for identifying a sip. As mentioned above, in addition to identifying a sip, the fluid intake module 126 estimates a liquid consumption metric for the user during the sip. The liquid consumption metric estimation is described in more detail with reference to FIG. 3C.

FIG. 3C illustrates example graphs of filtered sequences of orientation data 270 and 290 where each sequence is indicative of a sip. As described above, the liquid consumption metric may be an estimate of the number of sips taken by a user over a particular time interval, may be an estimate of the volume of liquid consumed, may be an indication of when the sips where taken, may be the frequency of sips taken, etc. In the example filtered sequences 270 and 290 of FIG. 3C, the liquid consumption metric is calculated as an estimate of the volume of liquid consumed. However, in other scenarios the liquid consumption metric may be an estimate of the number of sips taken by a user over a particular time interval.

The first sequence 270 corresponds to a volume of about 13 milliliters whereas the second sequence 290 corresponds to a volume of about 48 milliliters. The estimate of the volume may be based on sip characteristics such as the duration of the sip, the orientation of the sip, the slope of the orientation during the sip, the average orientation of the sip, and/or the ratio between the rising part of the sip, when the user tilts the bottle toward her mouth, and the falling part of the sip, when the user tilts the bottle away from her mouth and sets the bottle down (e.g., the time it takes to complete parts "a" and "b" of the sip as compared to the time it takes to complete part "c").

For example, a long sip or a sip when the bottle is nearly in the downright, vertical position may correspond to a large volume estimate. Moreover, when the orientation during the sip changes rapidly the volume estimate may be larger than the volume estimate when the orientation during the sip changes gradually (e.g., a user who tilts the bottle quickly while drinking water may drink more water than a user who tilts the bottle slowly or does not tilt it at all while he is drinking). Furthermore, the volume may be estimated based on previous sips taken by the user. For example, a sip when the bottle is nearly in the downright, vertical position may correspond to a large volume estimate when the bottle has been refilled just before the sip. On the other hand, when there have been several sips taken before the sip without a refill, then the volume estimate may be small even when the bottle is nearly in the downright, vertical position. This is because the fluid intake module 126 may determine that the bottle is nearly empty, and as a result, the bottle had to be tilted more to consume even a small amount of liquid. Additionally, any other suitable characteristics or combination of characteristics may also be considered when estimating the volume of the liquid consumed from the sip.

More specifically, the first sequence of orientation data 270 lasted 2.4 seconds from the time the user picked up the bottle 272 until the bottle was returned to the vertical, upright position 278. On the other hand, the second sequence 290 lasted 3.3 seconds from the time the user picked up the bottle 292 until the bottle was returned to the vertical, upright position 298. While this length of time may be used to approximate the duration of the sip, in some embodiments, the length of time from the beginning to the end of part "b" (where the orientation has a more gradual slope) as described in FIG. 3B, may also be used to approximate the duration of the sip. For example, for the first sequence 270, part "b" begins around 15.5 seconds 274 and ends around 16.5 seconds 276 for a duration of 1 second. Furthermore, the first sequence 270 has a height or maximum g-force of about 0.5 (reference 276), whereas the second sequence 290 has a height of about +1 (reference 296). Each of these sip characteristics may be aggregated and/or combined to estimate the volume of the liquid consumed from the sip. For example, these sip characteristics may be aggregated and/or combined to determine that the volume consumed in the first sequence 270 is less than the volume consumed in the second sequence 290.

Moreover, to determine more accurate estimates of the volume consumed, the sequences of orientation data 270 and 290 may be compared to previously recorded orientation data where the volume consumed may be known. For example, the orientation data may be analyzed to determine that 90% of the time the duration is 3.5 seconds and the maximum g-force is 0.7, the volume consumed is between 48 and 50 milliliters.

Additionally, in some embodiments, the fluid intake module 126 may include a training period where a user may input via the user interface, the volume of the liquid container. The fluid intake module 126 may aggregate each volume estimate between two consecutive refill events. If the aggregated volume estimate is similar to the volume of the liquid container then the fluid intake module 126 is likely estimating volume accurately. On the other hand, if the aggregated volume is not similar to the volume of the liquid container, the fluid intake module 126 may have to calibrate future volume estimates based on whether the estimate was too high, too low, etc.

Further, in some embodiments, the fluid intake module 126 may estimate the liquid consumption metric for the first sequence 270 and the second sequence 290 as the number of sips over a particular time interval. For example, the time interval may be one second. Therefore, for the first sequence 270 the liquid consumption metric may be estimated as one sip every 2.4 seconds or about 0.4 sips per second. For the second sequence 290 the liquid consumption metric may be estimated as one sip every 3.3 seconds or about 0.3 sips per second.

Figure 4:
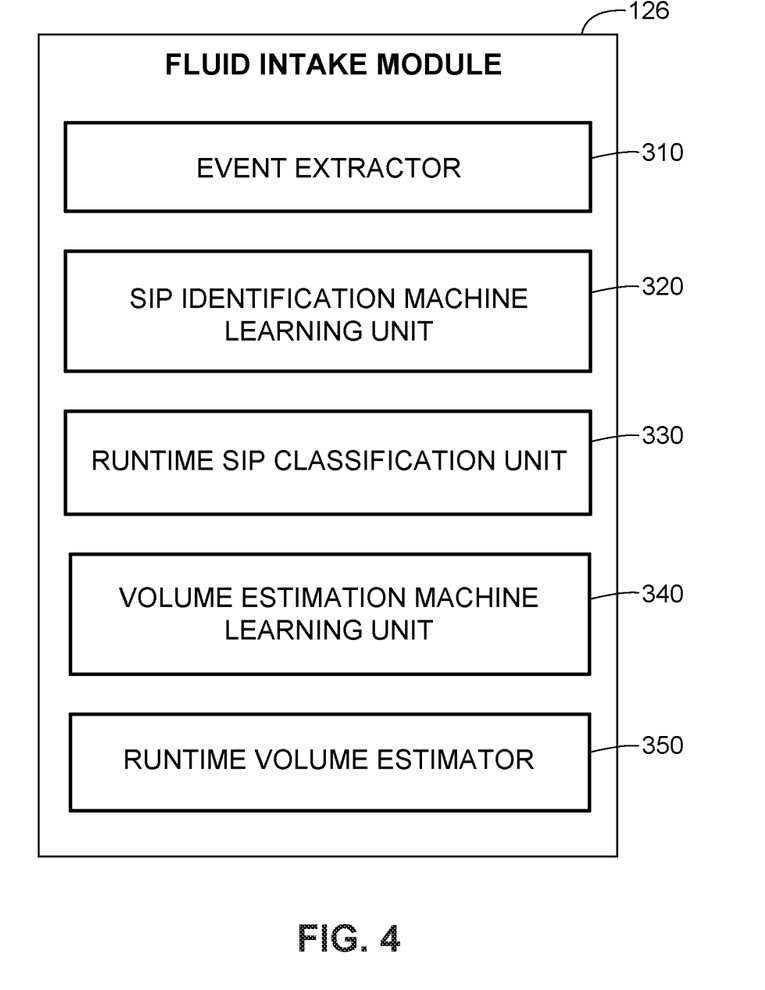
FIG. 4 depicts a block diagram detailing an example analysis of the measured orientations of a liquid container.

FIG. 4 depicts a block diagram detailing an example analysis of the measured orientation data for a liquid container by the fluid intake module 126 of FIG. 2. The fluid intake module 126 may include an event extractor 310, a sip identification machine learning unit 320, a runtime sip classification unit 330, a volume estimation machine learning unit 340, and a runtime volume estimator 350. The event extractor 310, sip identification machine learning unit 320, runtime sip classification unit 330, volume estimation machine learning unit 340, and runtime volume estimator 350 may be separate modules or may be combined and may interact with each other and/or with other software, hardware, and/or firmware.

The event extractor 310 may receive orientation data for a liquid container over a time interval such as the orientation data 200 of FIG. 3A. The event extractor 310 may receive the orientation data from the accelerometer 124, and filter the orientation data to obtain sequences of orientation data which differ from the default vertical, upright orientation having a g-force of −1. For example, the event extractor 310 may filter the orientation data 200 to obtain the filtered sequence 250 of FIG. 3B.

The sip identification machine learning unit 320 may receive and store a sip signature based on orientation patterns from previously recorded sips. The sip signature may be received from the server 140 of FIG. 2. In some embodiments, the machine learning module 146 within the server 140 may receive previously recorded sips from several users and analyze orientation patterns from the previously recorded sips to generate a sip signature. For example, the sip signature may be based on orientation data measured, during a training period, when users press and/or release a push-button switch connected to the smart band 10 to indicate that they are taking sips. The sip signature may then be transmitted to the sip identification machine learning unit 320. In some scenarios, the server 140 may continuously receive new orientation patterns and may update the sip signature accordingly. The updated sip signature may then be transmitted to the sip identification machine learning unit 320. In some embodiments, the sip signature may be stored in the sip signature data 127 of the smart band computing device 110.

In any event, in addition to receiving a sip signature, the sip identification machine learning unit 320 may update and/or modify the sip signature based on sips taken by the user of the smart band computing device 110. For example, the user's sips may be much shorter than the previously recorded sips from the several users. However, over time the machine learning unit 320 may store some of the user's orientation data, and determine that the user is taking sips despite their short duration because the user is constantly refilling the bottle.

Moreover, the sip identification machine learning unit 320 may also receive a refill signature based on orientation patterns from previously recorded refills. For example, a refill signature may include a much longer duration than a sip signature because of the time it takes to refill a bottle. Further, the maximum g-force may also be much lower compared to a sip signature, because the bottle may not need to be tilted as much for a refill.

The sip identification machine learning unit 320 may also include other identification information such as signatures for identifying walking, talking, or running while holding the bottle, running while the bottle is in a backpack, etc. Each of the sip signature, refill signature, walking signature, talking signature, and running signature may be generated, modified, and/or updated using one or several machine learning techniques (e.g., artificial neural networks, support vector machines, naïve Bayes, random forests, boosting, linear regression, logistic regression, k-nearest neighbors, decision trees, hidden Markov models, etc.). For example, sip signatures generated, modified, and/or updated using artificial neural networks may detect sips with 99 percent accuracy, while sip signatures generated, modified, and/or updated using support vector machines and naïve Bayes may detect sips with 96 percent accuracy and 92 percent accuracy, respectively. Accordingly, sip signatures generated, modified, and/or updated using any of artificial neural networks, support vector machines, and naïve Bayes may detect sips with over 90 percent accuracy. In other embodiments, the sip identification machine learning unit 320 may be included in the memory 144 of the server 140 and may receive orientation data from the smart band computing device 110.

The runtime sip classification unit 330 may then compare each of the filtered orientation data sequences to the sip signature, refill signature, walking, talking, or running signatures, etc., from the sip identification machine learning unit 320 to classify the filtered orientation data sequences. In some embodiments, some of the filtered orientation data sequences may not receive a classification. The runtime sip classification unit 330 may identify a filtered orientation data sequence which matches with the sip signature as a sip, and also may determine sip characteristics such as the length of time for sip, the maximum g-force for the sip, the slope of the orientation for the sip, etc.

In addition to the sip identification machine learning unit 320, the fluid intake module 126 may include a volume estimation machine learning unit 340. The volume estimation machine learning unit 340 may receive volume estimate data based on orientation patterns from previously recorded sips where the volume of the liquid consumed was known. The volume estimate data may be received from the server 140 of FIG. 2. In some embodiments, the machine learning module 146 within the server 140 may receive volume measurements of previously recorded sips from several users and analyze the correlation between the volume consumed and sip characteristics for the previously recorded sips such as duration, maximum g-force, orientation slope, etc. The machine learning module 146 may then determine an estimate of volume consumed based on the various sip characteristics. The estimate of volume consumed may then be transmitted to the volume estimation machine learning unit 340. In some scenarios, the server 140 may continuously receive new sip characteristics and may update the volume estimate accordingly. The updated volume estimate may then be transmitted to the volume estimation machine learning unit 320. In some embodiments, the volume estimate may be stored in the volume estimate data 127 of the smart band computing device 110.

In any event, in addition to receiving a volume estimate from the server 140, the volume estimation machine learning unit 340 may adjust and/or modify the volume estimate based on orientation data for the user of the smart band computing device 110. The volume estimation machine learning unit 340 may aggregate each volume estimate between two consecutive refill events. If the aggregated volume estimate is similar to the volume of the liquid container then the volume estimation machine learning unit 340 is likely estimating volume accurately. On the other hand, if the aggregated volume is not similar to the volume of the liquid container, the volume estimation machine learning unit 340 may have to calibrate future volume estimates based on whether the estimate was too high, too low, etc.

The volume estimate data may be generated, modified, and/or updated using one or several machine learning techniques (e.g., artificial neural networks, support vector machines, naïve Bayes, random forests, boosting, linear regression, logistic regression, k-nearest neighbors, decision trees, hidden Markov models, etc.). For example, volume estimate data generated, modified, and/or updated using support vector machines may estimate the volume of liquid consumed with 25 percent error, while volume estimate data generated using linear regression and artificial neural networks may estimate the volume of liquid consumed with 30 percent error and 32 percent error, respectively. In other embodiments, the volume estimation machine learning unit 340 may be included in the memory 144 of the server 140 and may receive orientation data from the smart band computing device 110.

The runtime volume estimator 350 then compares sip characteristics of the sips identified by the runtime sip classification unit 330 to sip characteristics for volume estimates from the volume estimation machine learning unit 340 to estimate the volume of liquid consumed for each sip. For example, the volume estimation machine learning unit 340 may determine that 95% of the time the duration for a sip is 2 seconds, the maximum g-force is 0.5, and the slope of the orientation during the sip is between 0.8 and 1.2, the volume consumed is between 18 and 20 milliliters. As a result, the runtime volume estimator may estimate that a sip having matching sip characteristics corresponds to a volume of 19 milliliters. The runtime volume estimator 350 may also aggregate each estimated volume to determine an overall volume estimate over a particular time interval. This overall volume estimate may be displayed on the user interface of the smart band computing device 110 to let the user know how much she is drinking. While the runtime volume estimator 350 may estimate the volume of liquid consumed, this is merely one way to calculate the liquid consumption metric. In other embodiments, the liquid consumption metric may be based on the accumulating estimated amount of sips taken over a period of time, when the sips where taken, the frequency of sips taken, etc.

Figure 5:
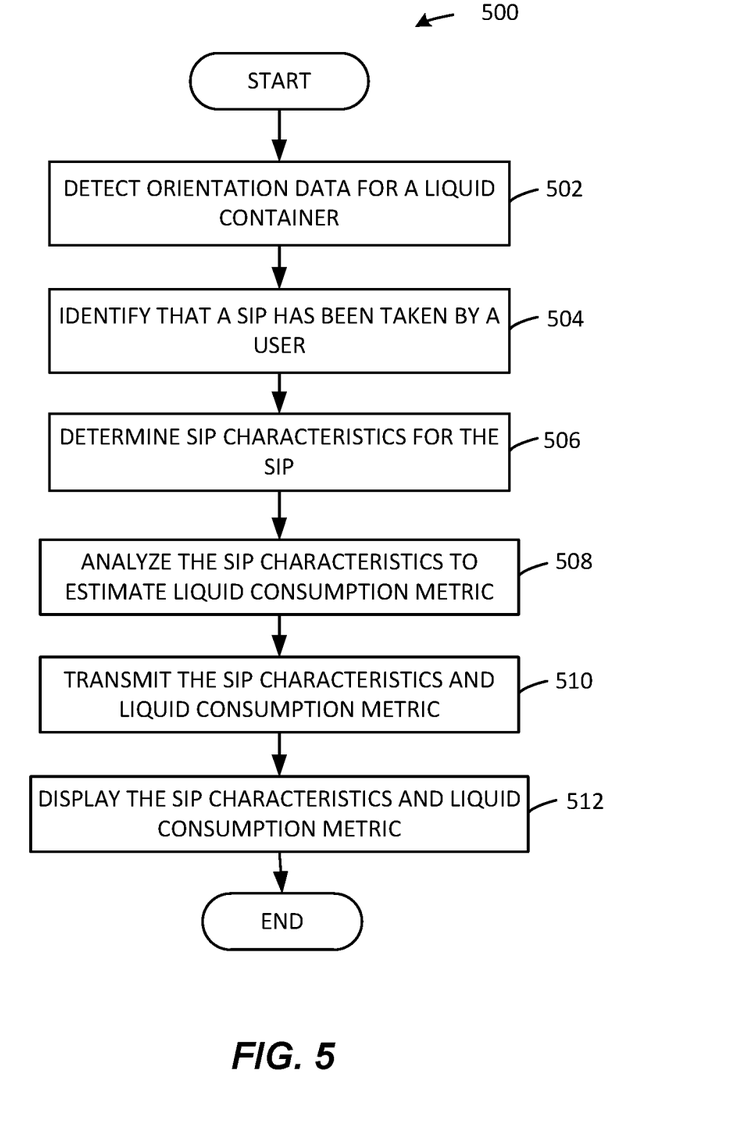
FIG. 5 illustrates a flow diagram representing an example method for determining a user's fluid intake in accordance with the presently described embodiments.

FIG. 5 illustrates a flow diagram representing an example method 500 for determining a user's fluid intake. The method 500 may be executed on the smart band computing device 110, the server computer 140, or some combination of the smart band computing device 110 and the server computer 140. For example, at least a portion of the method 500 may be performed by the fluid intake module 126 of FIG. 2 which is disposed within the smart band computing device 110. In an embodiment, the fluid intake module 126 may include computer-executable instructions stored on one or more non-transitory, tangible, computer-readable storage media or devices, and the computer-executable instructions of the fluid intake module 126 may be executed to perform the method 500.

At block 502, orientation data for a liquid container may be detected. The orientation data may be measured by an accelerometer disposed within the smart band computing device 110 and sent to the fluid intake module 126. Each orientation may correspond to an instance of time and may be represented by an acceleration, for example, a g-force. Then at block 504, the fluid intake module 126 may identify that a sip has been taken by the user based on the orientation data. A sip may be identified by comparing the orientation data to previous orientation data indicative of a sip such as a sip signature. If a matching sip signature is identified in the orientation data, then the matching sip signature is indicative of a sip. The sip signature may be received from the server 140 and stored at the fluid intake module 126. In some embodiments, the previous orientation data may be obtained at the server 140 from several users drinking from several types of liquid containers.

At block 506, the identified sip is analyzed to determine sip characteristics such as the length of time for the sip, the maximum g-force of the sip, the slope of the orientation of the sip, etc. The sip characteristics are then analyzed at a block 508 to estimate a liquid consumption metric for the sip (e.g., the estimated volume of liquid consumed, the accumulating estimated amount of sips taken over a period of time, when the sips where taken, the frequency of sips taken, etc.). The liquid consumption metric may be based on the number of sips per unit time and/or the volume consumed by the user during the sip, which may also be determined at the block 508. Similar to block 504, the liquid consumption metric is estimated by comparing sip characteristics to a set of previous sip characteristics corresponding to a particular volume. If the sip characteristics are similar to a set of previous sip characteristics, then the liquid consumption metric may be estimated based on the corresponding volume for the set of previous sip characteristics. For example, if the sip characteristics are similar to a set of previous sip characteristics corresponding to a volume between 36 and 42 milliliters, then the volume estimate for the sip may be 36 milliliters, 40 milliliters, 42 milliliters, etc. Further, in some embodiments, the liquid consumption metric may by estimated by aggregating the total number of sips taken over a time interval and/or dividing the number of sips by the time interval.

At block 510, the fluid intake data including the sip, the sip characteristics, and/or the liquid consumption metric may be transmitted to a Bluetooth connected smart phone or any other network-enabled device. The fluid intake data may be stored on the smart phone for later viewing by the user, and the smart phone may also transmit the information via a communication network to the server 140. The server 140 may store the fluid intake data so that the user can access this information on a network-enabled device. This information may also be stored at the server 140 for further analysis and machine learning to improve the accuracy of the sip identification and the volume estimates.

In addition to transmitting the fluid intake data to a network-enabled device, at block 512, the fluid intake module 126 may display the fluid intake data on the user interface of the smart band computing device 110. The liquid consumption metric may also be aggregated with previous liquid consumption metrics to display a total number of sips over a particular time interval and/or an estimate of the volume consumed by the user over that time interval. The user interface may also display the number of refills detected over the time interval, an indication of the volume of the liquid container being used, the number of liquid containers used over the time interval, etc.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as providing examples only and does not describe every possible embodiment, as describing every possible embodiment would be impractical, if not impossible. One could implement numerous alternate embodiments, using either current technology or technology developed after the filing date of this application.

We claim:

1. A method for tracking liquid consumption, the method comprising:
   detecting, by one or more processors, one or more orientations of a liquid container;
   identifying that a sip from the liquid container has been taken by a user based on a sip signature identified according to the detected one or more orientations of the liquid container, the sip signature determined based on a plurality of sips from a plurality of other users;
   identifying one or more characteristics of the sip;
   analyzing the identified sip and the one or more characteristics of the sip to determine an estimate of a liquid consumption metric for the user; and
   transmitting the identified sip and the one or more characteristics of the sip to one or more computing devices via a communication network for storage.

2. The method of claim 1, wherein detecting one or more orientations of a liquid container comprises detecting acceleration data for the liquid container via an accelerometer.

3. The method of claim 2, further comprising:
   filtering the detected acceleration data for the liquid container to obtain data including one or more orientations of the liquid container which differs from a default orientation.

4. The method of claim 1, wherein one or more characteristics of the sip includes at least one of: a duration of the sip, a maximum orientation for the sip, a slope of the orientation during the sip, an average orientation for the sip, or a ratio between a rising part of the sip and a falling part of the sip.

5. The method of claim 1, wherein identifying that a sip has been taken comprises identifying that a plurality of sips have been taken and wherein analyzing the identified sip and the one or more characteristics of the sip to determine an estimate of a liquid consumption metric for the user comprises:
   for each of the plurality of sips, determining an estimate of a volume of liquid consumed by the user based on the one or more orientations of the liquid container corresponding to the sip and the one or more characteristics of the sip;
   aggregating one or more estimates of the volume of the liquid consumed by the user for each identified sip until the refill event is detected;
   comparing the aggregated estimate of the volume to a volume of the liquid container; and
   training for future volume estimates based on a difference between the aggregated estimate of the volume and the actual volume of the liquid container.

6. The method of claim 1, wherein identifying that a sip has been taken comprises identifying that a plurality of sips have been taken and wherein analyzing the identified sip and the one or more characteristics of the sip to determine an estimate of a liquid consumption metric for the user comprises:
   aggregating each of the plurality of sips to determine an overall number of sips over a time interval; and
   determining the estimate of the liquid consumption metric based on the overall number sips over the time interval.

7. The method of claim 1, wherein the sip signature comprises:
   (i) an increase in acceleration of the liquid container, (ii) a constant acceleration of the liquid container, and (iii) a decrease in acceleration of the liquid container.

8. The method of claim 1, further comprising:
   displaying the estimate of the liquid consumption metric for the user on a user interface.

9. A system for tracking liquid consumption of a liquid container, the system comprising:
   a communication interface; and
   one or more computing devices communicatively coupled to the communication interface, each of the one or more computing devices having a memory and one or more processors and the one or more computing devices configured to:
      detect an indication of one or more orientations of a liquid container;
      identify that a sip from the liquid container has been taken by a user based on a sip signature identified according to the detected one or more orientations of the liquid container, the sip signature determined based on a plurality of sips from plurality of other users;
      identify one or more characteristics of the sip;
      analyze the identified sip and the one or more characteristics of the sip to determine an estimate of a liquid consumption metric for the user; and
      transmit the sip identification information and the one or more characteristics of the sip to one or more server computing devices via the communication interface for storage.

10. The system of claim 9, further comprising an accelerometer, wherein the one or more computing devices are further configured to detect the one or more orientations of the liquid container based on acceleration data from the accelerometer.

11. The system of claim 10, wherein the one or more computing devices are further configured to:
   filter the detected acceleration data for the liquid container to obtain data including one or more orientations of the liquid container which differs from a default orientation.

12. The system of claim 9, wherein the one or more characteristics of the sip includes at least one of: a duration of the sip, a maximum orientation for the sip, a slope of the orientation during the sip, an average orientation for the sip, or a ratio between a rising part of the sip and a falling part of the sip.

13. The system of claim 9, wherein a sip comprises a plurality of sips and wherein to analyze the identified sip and the one or more characteristics of the sip to determine an estimate of a liquid consumption metric for the user, the one or more computing devices are configured to:
   for each of the plurality of sips, determine an estimate of a volume of liquid consumed by the user based on the one or more orientations of the liquid container corresponding to the sip and the one or more characteristics of the sip;
   aggregate one or more estimates of the volume of the liquid consumed by the user for each identified sip until the refill event is detected;
   compare the aggregated estimate of the volume to a volume of the liquid container; and
   train for future volume estimates based on a difference between the aggregated estimate of the volume and the actual volume of the liquid container.

14. The system of claim 9, wherein a sip comprises a plurality of sips and wherein to analyze the identified sip and the one or more characteristics of the sip to determine an estimate of a liquid consumption metric for the user, the one or more computing devices are configured to:
   aggregate each of the plurality of sips to determine an overall number of sips over a time interval; and
   determine the estimate of the liquid consumption metric based on the overall number sips over the time interval.

15. The system of claim 9, wherein the sip signature comprises:
   (i) an increase in acceleration of the liquid container, (ii) a constant acceleration of the liquid container, and (iii) a decrease in acceleration of the liquid container.

16. The system of claim 9, further comprising a user interface, wherein the one or more computing devices are further configured to display the estimate of the liquid consumption metric for the user on the user interface.

* * * * *